(12) United States Patent
Corbin et al.

(10) Patent No.: US 10,013,292 B2
(45) Date of Patent: Jul. 3, 2018

(54) SYSTEM AND METHOD FOR DYNAMIC METADATA PERSISTENCE AND CORRELATION ON API TRANSACTIONS

(71) Applicant: PokitDok, Inc., San Mateo, CA (US)

(72) Inventors: Brian Corbin, San Mateo, CA (US); Tim Dunlevy, San Mateo, CA (US); Denise K. Gosnell, San Mateo, CA (US); Matt Aldridge, San Mateo, CA (US); Doug Thomas, San Mateo, CA (US); Ted Tanner, San Mateo, CA (US)

(73) Assignee: POKITDOK, INC., San Mateo, CA (US)

( * ) Notice: Subject to any disclaimer, the term of this patent is extended or adjusted under 35 U.S.C. 154(b) by 0 days.

(21) Appl. No.: 15/294,341

(22) Filed: Oct. 14, 2016

(65) Prior Publication Data

US 2017/0109218 A1 Apr. 20, 2017

Related U.S. Application Data

(60) Provisional application No. 62/242,253, filed on Oct. 15, 2015.

(51) Int. Cl.
| | |
|---|---|
| *G06F 9/44* | (2018.01) |
| *G06F 9/54* | (2006.01) |
| *G06F 17/30* | (2006.01) |
| *G16H 10/60* | (2018.01) |

(52) U.S. Cl.
CPC ........ *G06F 9/541* (2013.01); *G06F 17/30958* (2013.01); *G16H 10/60* (2018.01)

(58) Field of Classification Search
CPC ...................................................... G06F 9/541

USPC .......................................................... 719/328
See application file for complete search history.

(56) References Cited

U.S. PATENT DOCUMENTS

| | | |
|---|---|---|
| 5,872,021 A | 2/1999 | Matsumoto et al. |
| 6,546,428 B2 | 4/2003 | Baber et al. |
| 7,386,565 B1 | 6/2008 | Singh et al. |
| 7,917,378 B2 | 3/2011 | Fitzgerald et al. |
| 7,917,515 B1 | 3/2011 | Lemoine |
| 7,970,802 B2 | 6/2011 | Ishizaki |
| 7,992,153 B2 | 8/2011 | Ban |
| 8,073,801 B1 | 12/2011 | Von Halle et al. |
| 8,095,975 B2 | 1/2012 | Boss et al. |
| 8,103,667 B2 | 1/2012 | Azar et al. |

(Continued)

FOREIGN PATENT DOCUMENTS

| | | |
|---|---|---|
| GB | 2478440 | 10/2013 |
| WO | WO 2012/122065 | 9/2012 |

OTHER PUBLICATIONS

Ahlswede et al., *Network Information Flow*, IEEE Transactions on Information Theory, vol. 46, No. 4; Jul. 2000 (13 pgs.).

(Continued)

*Primary Examiner* — Andy Ho
(74) *Attorney, Agent, or Firm* — DLA Piper LLP (US)

(57) ABSTRACT

A dynamic metadata persistence and correlation system and method are disclosed. The system and method provide a means of tracking and relating transactional metadata from application API calls to internal data models. This system pairs application level flexibility with dynamic correlation management for entity evolution, data retrieval, and analytics.

10 Claims, 8 Drawing Sheets

(56) References Cited

U.S. PATENT DOCUMENTS

| | | | |
|---|---|---|---|
| 8,103,952 B2 | 1/2012 | Hopp | |
| 8,203,562 B1 | 6/2012 | Alben et al. | |
| 8,229,808 B1 | 7/2012 | Heit | |
| 8,286,191 B2 | 10/2012 | Amini et al. | |
| 8,359,298 B2 | 1/2013 | Schacher et al. | |
| 8,364,501 B2 | 1/2013 | Rana et al. | |
| 8,417,755 B1 | 4/2013 | Zimmer | |
| 8,495,108 B2 | 7/2013 | Nagpal et al. | |
| 8,515,777 B1 | 8/2013 | Rajasenan | |
| 8,817,665 B2 | 8/2014 | Thubert et al. | |
| 8,984,464 B1 | 3/2015 | Mihal et al. | |
| 9,165,045 B2 | 10/2015 | Mok et al. | |
| 9,208,284 B1* | 12/2015 | Douglass | G06F 19/322 |
| 2002/0022973 A1 | 2/2002 | Sun et al. | |
| 2002/0038233 A1 | 3/2002 | Shubov et al. | |
| 2002/0165738 A1 | 11/2002 | Dang | |
| 2003/0097359 A1 | 5/2003 | Ruediger | |
| 2003/0171953 A1 | 9/2003 | Narayanan et al. | |
| 2003/0217159 A1 | 11/2003 | Schramm-Apple et al. | |
| 2003/0233252 A1 | 12/2003 | Haskell et al. | |
| 2004/0143446 A1 | 7/2004 | Lawrence | |
| 2005/0010452 A1 | 1/2005 | Lusen | |
| 2005/0071189 A1 | 3/2005 | Blake et al. | |
| 2005/0102170 A1 | 5/2005 | Lefever et al. | |
| 2005/0137912 A1 | 6/2005 | Rao et al. | |
| 2005/0152520 A1 | 7/2005 | Logue | |
| 2005/0182780 A1 | 8/2005 | Forman et al. | |
| 2005/0222912 A1 | 10/2005 | Chambers | |
| 2006/0036478 A1 | 2/2006 | Aleynikov et al. | |
| 2006/0074290 A1 | 4/2006 | Chen et al. | |
| 2006/0089862 A1 | 4/2006 | Anandarao et al. | |
| 2006/0129428 A1 | 6/2006 | Wennberg | |
| 2006/0136264 A1 | 6/2006 | Eaton et al. | |
| 2007/0113172 A1 | 5/2007 | Behrens et al. | |
| 2007/0118399 A1 | 5/2007 | Avinash et al. | |
| 2007/0156455 A1 | 7/2007 | Tarino et al. | |
| 2007/0180451 A1 | 8/2007 | Ryan et al. | |
| 2007/0214133 A1 | 9/2007 | Liberty et al. | |
| 2007/0233603 A1 | 10/2007 | Schmidgall et al. | |
| 2007/0260492 A1 | 11/2007 | Feied et al. | |
| 2007/0276858 A1 | 11/2007 | Cushman et al. | |
| 2007/0288262 A1 | 12/2007 | Sakaue et al. | |
| 2008/0013808 A1 | 1/2008 | Russo et al. | |
| 2008/0082980 A1 | 4/2008 | Nessland et al. | |
| 2008/0091592 A1 | 4/2008 | Blackburn et al. | |
| 2008/0126264 A1 | 5/2008 | Tellefsen et al. | |
| 2008/0133436 A1 | 6/2008 | Di Profio | |
| 2008/0288292 A1 | 11/2008 | Bi et al. | |
| 2008/0295094 A1 | 11/2008 | Korupolu et al. | |
| 2009/0125796 A1 | 5/2009 | Day et al. | |
| 2009/0192864 A1 | 7/2009 | Song et al. | |
| 2009/0198520 A1 | 8/2009 | Piovanetti-Perez | |
| 2009/0300054 A1 | 12/2009 | Fisher et al. | |
| 2009/0307104 A1 | 12/2009 | Weng | |
| 2009/0313045 A1 | 12/2009 | Boyce | |
| 2010/0076950 A1 | 3/2010 | Kenedy et al. | |
| 2010/0082620 A1 | 4/2010 | Jennings, III et al. | |
| 2010/0088108 A1 | 4/2010 | Machado | |
| 2010/0088119 A1 | 4/2010 | Tipirneni | |
| 2010/0138243 A1 | 6/2010 | Carroll | |
| 2010/0217973 A1 | 8/2010 | Kress et al. | |
| 2010/0228721 A1 | 9/2010 | Mok et al. | |
| 2010/0295674 A1 | 11/2010 | Hsieh et al. | |
| 2010/0332273 A1 | 12/2010 | Balasubramanian et al. | |
| 2011/0015947 A1 | 1/2011 | Erry et al. | |
| 2011/0055252 A1 | 3/2011 | Kapochunas et al. | |
| 2011/0071857 A1 | 3/2011 | Malov et al. | |
| 2011/0137672 A1 | 6/2011 | Adams et al. | |
| 2011/0218827 A1 | 9/2011 | Kennefick et al. | |
| 2011/0270625 A1 | 11/2011 | Pederson et al. | |
| 2012/0011029 A1 | 1/2012 | Thomas | |
| 2012/0035984 A1 | 2/2012 | Srinivasa et al. | |
| 2012/0078940 A1 | 3/2012 | Kolluri et al. | |
| 2012/0130736 A1 | 5/2012 | Dunston et al. | |
| 2012/0158429 A1 | 6/2012 | Murawski et al. | |
| 2012/0158750 A1 | 6/2012 | Faulkner et al. | |
| 2012/0173279 A1 | 7/2012 | Nessa et al. | |
| 2012/0245958 A1 | 9/2012 | Lawrence et al. | |
| 2012/0246727 A1 | 9/2012 | Elovici et al. | |
| 2012/0290320 A1 | 11/2012 | Kurgan et al. | |
| 2012/0290564 A1 | 11/2012 | Mok et al. | |
| 2013/0030827 A1 | 1/2013 | Snyder et al. | |
| 2013/0044749 A1 | 2/2013 | Eisner et al. | |
| 2013/0085769 A1 | 4/2013 | Jost et al. | |
| 2013/0138554 A1 | 5/2013 | Nikankin et al. | |
| 2013/0166552 A1 | 6/2013 | Rozenwald et al. | |
| 2013/0204940 A1 | 8/2013 | Kinsel et al. | |
| 2013/0304903 A1 | 11/2013 | Mick et al. | |
| 2014/0046931 A1 | 2/2014 | Mok et al. | |
| 2014/0056243 A1 | 2/2014 | Pelletier et al. | |
| 2014/0059084 A1 | 2/2014 | Adams et al. | |
| 2014/0088981 A1 | 3/2014 | Momita | |
| 2014/0136233 A1 | 5/2014 | Atkinson et al. | |
| 2014/0244300 A1 | 8/2014 | Bess et al. | |
| 2014/0278491 A1 | 9/2014 | Weiss | |
| 2014/0358578 A1 | 12/2014 | Ptachcinski | |
| 2014/0358845 A1 | 12/2014 | Mundlapudi et al. | |
| 2015/0095056 A1 | 4/2015 | Ryan et al. | |
| 2015/0112696 A1 | 4/2015 | Kharraz Tavakol | |
| 2015/0142464 A1 | 5/2015 | Rusin et al. | |
| 2015/0199482 A1 | 7/2015 | Corbin et al. | |
| 2015/0332283 A1 | 11/2015 | Witchey | |
| 2016/0028552 A1 | 1/2016 | Spanos et al. | |
| 2016/0055205 A1 | 2/2016 | Jonathan et al. | |
| 2016/0253679 A1* | 9/2016 | Venkatraman | G06Q 50/184 |
| 2016/0328641 A1* | 11/2016 | AlSaud | G06N 3/0436 |
| 2017/0091397 A1 | 3/2017 | Shah et al. | |
| 2017/0132621 A1 | 5/2017 | Miller et al. | |

OTHER PUBLICATIONS

Bhattacharya, Indrajit and Getoor, Lise, *Entity Resolution in Graphs*, Department of Computer Science, University of Maryland (2005) (21 pgs.).

Chen et al., *Adaptive Graphical Approach to Entity Resolution*, Jun. 18-23, 2007, Proceedings of the 7th ACM/IEEE-CS Joint Conference on Digital Libraries, pp. 204-213 (10 pgs.).

Christen, *Data Matching, Concepts and Techniques for Record Linkage, Entity Resolution, and Duplicate Detection*, © Springer-Verlag Berlin Heidelberg, 2012 (279 pgs.).

Cohen et al., *A Comparison of String Metrics for Matching Names and Records*, © 2003, American Association for Artificial Intelligence (www.aaai.org) (6 pgs.).

Coleman et al., Medical Innovation—a diffusion study; The Bobbs-Merrill Company, Inc., 1966 (248 pgs.).

Domingos et al., Mining High-Speed Data Streams, (2000) (10 pgs.).

Greenhalgh et al., Diffusion of Innovations in Health Service Organisations—a systematic literature review, Blackwell Publishing, 2005 (325 pgs.).

Jackson et al., The Evolution of Social and Economic Networks, Journal of Economic Theory 106, pp. 265-295, 2002 (31 pgs.).

Jackson, Matthew O., Social and Economic Networks, Princeton University Press, 2008 (509 pgs.).

Krempl et al., Open Challenges for Data Stream Mining Research, SIGKDD Explorations, vol. 16, Issue 1, Jun. 2014 (64 pgs.).

Lin et al., A simplicial complex, a hypergraph, structure in the latent semantic space of document clustering, © Elsevier, 2005 (26 pgs.).

Mathjax, Naive Bayes Categorisation (with some help from Elasticsearch), blog post dated Dec. 29, 2013 (https://blog.wtf.sg/2013/12/29/naive-bayes-categorisation-with-some-help-from-elasticsearch/). (8 pgs.).

Newman, Modularity and community structure in networks, PNAS, vol. 103, No. 23, pp. 8581-8582 Jun. 6, 2006 (2 pgs.).

Rebuge, Business Process Analysis in Healthcare Environments, 2011, Ellsevier Ltd., pp. 99-116 (18 pgs.).

Titan Database Documentation ©2015 (disclosed at http://s3.thinkaurelius.com/docs/titan/1.0.0/ (printed Sep. 16, 2016) (214 pgs.).

(56) References Cited

OTHER PUBLICATIONS

Wasserman et al., *Social Network Analysis: Methods and Applications*, Cambridge University Press; 1994 (434 pgs.).
White et al., *Algorithms for Estimating Relative Importance in Networks*, Proceedings of the Ninth ACM SIGKDD International Conference on Knowledge Discovery and Data Mining, 2003 (10 pgs.).
Webpage: New Health Care Electronic Transactions Standards Versions 5010, D.0, and 3.0, Jan. 2010 ICN 903192; http://www.cms.gov/Regulations-and-Guidance/HIPAA-Adminstrative-Simplification/Versions5010and D0/downloads/w5010BasicsFctCht.pdf (4 pgs.).
Webpage: U.S. Dept. of Health and Human Services, Guidance Regarding Methods for De-identification of Protected Health Information in Accordance with the Health Insurance Portability and Accountability Act (HIPAA) Privacy Rule, http://www.hhs.gov/ocr/privacy/hipaa/understanding/coveredentities/De-identification/guidance.html printed Oct. 15, 2015 (14 pgs.).
Version 5010 and D.0, Center for Medicare and Medicaid Services (2 pgs.).
Anonymous: "Oauth" Wikipedia—Retrieved from the Internet URL:https://en.wikipedia.org/wiki/Oauth (8 pgs.).
Lin et al., A simplicial complex, a hypergraph, structure in the latent semantic space of document clustering, © 2005 Elsevier Inc. (26 pgs.).
Anonymous: "Oauth—Wikipedia", Sep. 23, 2013. Retrieved from the Internet URL:https://en.wikipedia.org/w/index.php?title+oAuth &oldid+574187532 (3 pages).
White, Scott et al.; "Algorithms for Estimating Relative Importance in Networks"; Proceedings of the ninth ACM SIGKDD international conference on Knowledge discovery and data mining; dated 2003 (10 pgs.).

\* cited by examiner

```
{
    "IEA": {
        "segment": [
            ....
        ]
    },
    "ISA": {
        "segment": [
            ....
        ]
    },
    "element_delimiter": "*",
    "field_separator": ":",
    "functional_groups": [
        ......
    ],
    "repetition_symbol": "^",
    "x12_transaction": "837",
    "application_data": [
        {
            "activity_id": "2KU1JCLRTNSWJTHZCNA",
            "patient_id": "9fd77995-6f62-49f4-bc65-09ddb7f2649e-0",
            "provider_id": "5ba823cd-5d8f-4a0c-b7af-8b65651f3a52-0",
            "other_data": "{\"notification_id\":
                \"4319e686-1a10-4178-8d48-2f9733f41f9d-0\", \"filename_prefix\":
                \"20150909090909_TEST_PROVIDER_5561ecb6-7e6f-4867-ba12-a7e09b45_837_\"}",
            "site_id": "b6f7021e-9654-431c-9943-efa2fd902291-0",
            "visit_id": "5561ecb6-7e6f-4867-ba12-a7e09b457620-9"
        }
    ]
}
```

FIGURE 5

SYSTEM AND METHOD FOR DYNAMIC METADATA PERSISTENCE AND CORRELATION ON API TRANSACTIONS

PRIORITY CLAIMS/RELATED APPLICATIONS

This application claims priority under 35 USC 120 to and claims the benefit under 35 USC 119(e) to U.S. Provisional Patent Application Ser. No. 62/242,253, filed Oct. 15, 2015 and entitled "System And Method For Dynamic Metadata Persistence And Correlation On API Transactions", the entirety of which is incorporated herein by reference.

FIELD

The disclosure relates generally to tracking and relating transactional metadata from application API calls to internal data models.

BACKGROUND

Application level API calls may require a level of user flexibility in order to fully encapsulate the data of each request. Additionally, each API call contains transaction data which details the specifics of the data exchange. Both the application level API calls and transaction metadata dynamically create data keys for transfer and persistence into a database. It is desirable to provide to provide a mechanism to facilitate the transfer, persistence and correlation of the application data and the API transactional metadata.

BRIEF DESCRIPTION OF THE DRAWINGS

FIG. 5 illustrates a level to which application level users can provide custom fields for persistence in the graph database;

DETAILED DESCRIPTION OF ONE OR MORE EMBODIMENTS

The disclosure is particularly applicable to a data persistence system and method that is used with the PokitDok healthcare system and method and its database shown in FIG. 1 and it is in this context that the disclosure will be described. It will be appreciated, however, that the system and method has greater utility since it may be used as a standalone system and it may be used with or integrated into other data systems in which it is desirable to facilitate the transfer, persistence and correlation of the application data and the API transactional metadata.

Application level API calls through the PokitDok platform require a level of user flexibility in order to fully encapsulate the data of each request. Additionally, each API call contains transaction data which details the specifics of the data exchange. Both the application level API calls and transaction metadata dynamically create data keys for transfer and persistence into a database. The system and method herein details the transfer, persistence and correlation of a dynamic set of application specific data in addition to API transaction metadata.

The dynamic metadata persistence and correlation system described below provides a means of tracking and relating transactional metadata from application API calls to internal data models. This system pairs application level flexibility with dynamic correlation management for entity evolution, data retrieval, and analytics.

Figure 1:
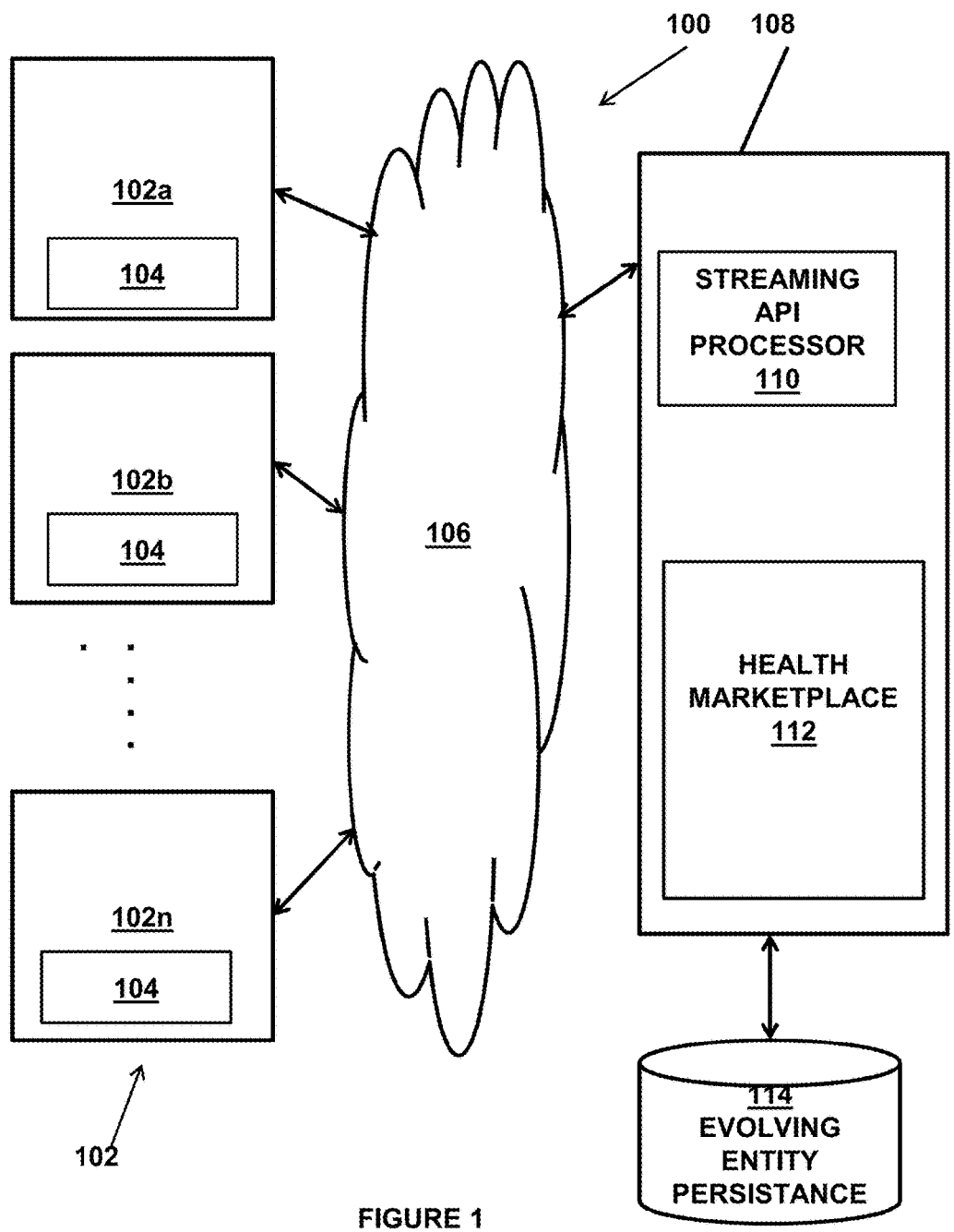
FIG. 1 illustrates an example of a healthcare system that may incorporate a data persistence system.

FIG. 1 illustrates an example of a healthcare system 100 that may incorporate a data persistence system that may be implemented in a backend component 108 or a health graph store 114 or in a combination of the backend component 108 and the heath graph store 114. The healthcare marketplace system 100 may have one or more computing devices 102 that connect over a communication path 106 to a backend system 108. Each computing device 102, such as computing devices 102a, 102b, . . . , 102n as shown in FIG. 1, may be a processor based device with memory, persistent storage, wired or wireless communication circuits and a display that allows each computing device to connect to and couple over the communication path 106 to a backend system 108. For example, each computing device may be a smartphone device, such as an Apple Computer product, Android OS based product, etc., a tablet computer, a personal computer, a terminal device, a laptop computer and the like. In one embodiment shown in FIG. 12, each computing device 102 may store an application 104 in memory and then execute that application using the processor of the computing device to interface with the backend system. For example, the application may be a typical browser application or may be a mobile application. The communication path 106 may be a wired or wireless communication path that uses a secure protocol or an unsecure protocol. For example, the communication path 106 may be the Internet, Ethernet, a wireless data network, a cellular digital data network, a WiFi network and the like.

The backend system 108 may also have an API processor component 110 and a health marketplace engine 112 that may be coupled together. Each of these components of the backend system may be implemented using one or more computing resources, such as one or more server computers, one or more cloud computing resources and the like. In one embodiment, the API processor 110 and health marketplace engine 112 may each be implemented in software in which each has a plurality of lines of computer code that are executed by a processor of the one or more computing resources of the backend system. In other embodiments, each of the API processor 110 and health marketplace engine 112 may be implemented in hardware such as a programmed logic device, a programmed processor or microcontroller and the like. The backend system 108 may be coupled to a health graph store 114 that stores the various data and software modules that make up the healthcare system as well as the health graph database that is used to store the health data of the backend component 108. The store 114 may be implemented as a hardware database system, a software database system or any other storage system. In this example implementation, the data persistence system may be incorporated into the backend system 108 or may be coupled to the backend system 108, but located remotely.

The API processor 110 may receive application programming interface (API) requests and communications from an application 104 of one of the computing devices 102 and may in part perform the data persistence process described below with reference to FIGS. 4-5. The health marketplace engine 112 may allow practitioners that have joined the healthcare social community to reach potential clients in ways unimaginable even a few years ago. In addition to giving practitioners a social portal with which to communicate and market themselves with consumers, the marketplace gives each healthcare practitioner the ability to offer their services in an environment that is familiar to users of Groupon, Living Social, or other social marketplaces.

In the system 100, each of the entries for a user may be stored in the store 114 in the health graph with a user's globally unique identifier and the identifiers of other users of the healthcare system that are allowed to view the information to provide, among other things, access control for the data in the healthstream of each user. In the system, each entry may default to being private among the users explicitly specified on the data. Users can choose to change the privacy level to 'anonymous' when they want to share information they've learned about a particular health issue with the community without revealing their identity.

Figure 2:
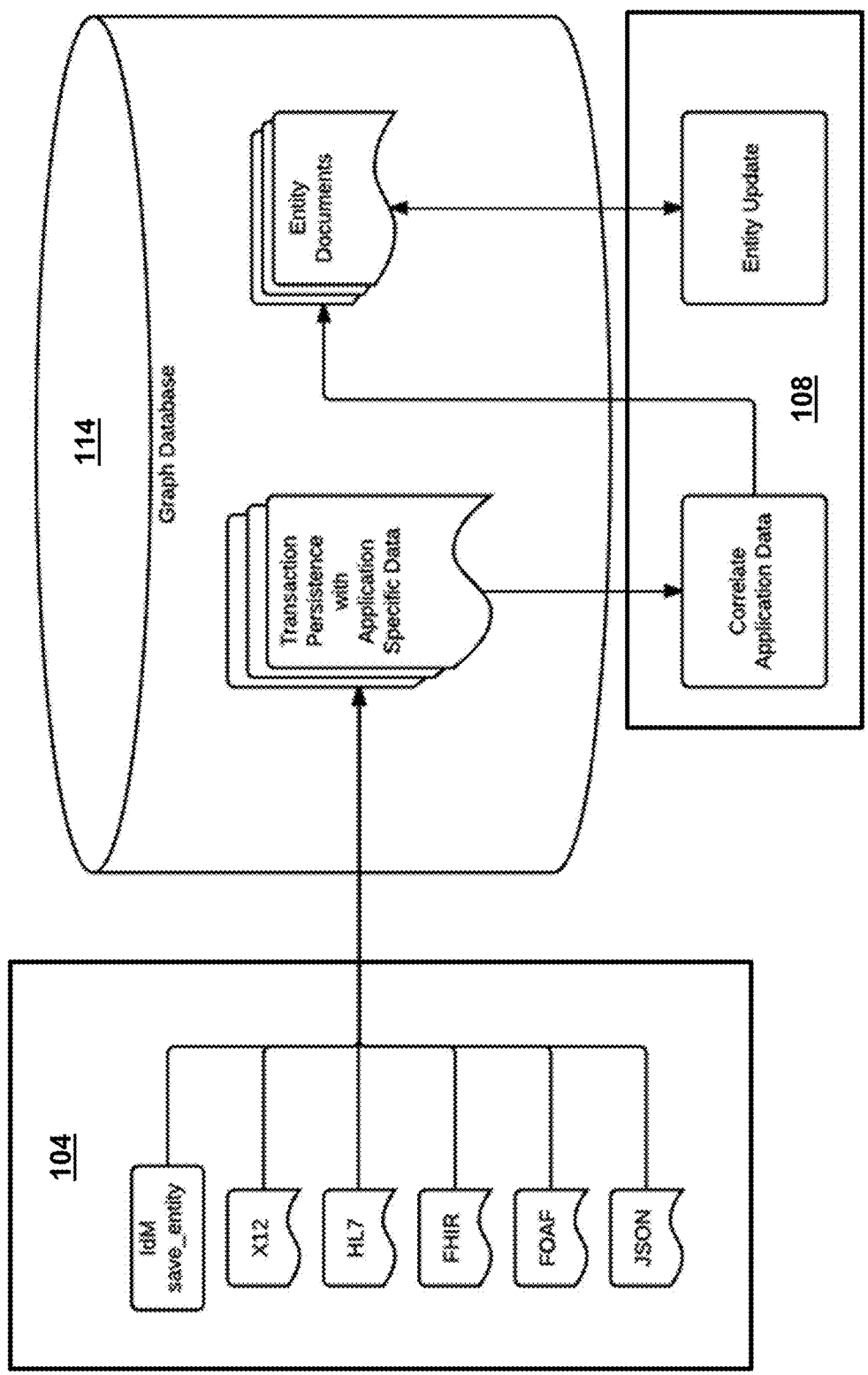
FIG. 2 illustrates an example of an implementation of a data persistence system.

FIG. 2 illustrates an example of an implementation of a data persistence system that may be implemented in the backend 108 and/or the store 114 depending on the particular implementation of the data persistence system. In the data persistence system, a piece of dynamic and flexible application level data enters the system through an API call from an application 104 being executed by one of the computing devices 102 as shown in FIG. 2. An example of the API call and the application level data that is contained in the API call is shown in FIG. 5. As shown in FIG. 2, the piece of data may be various types of data in various formats, such as save_entity data, X12 health data, HL7 data (described in more detail at www.hl7.org/implement/standards which is incorporated herein by reference), FHIR data (described in more detail at https://en.wikipedia.org/wiki/Fast_Healthcare_Interoperability_Resources which is incorporated herein by reference), FOAF data (described in more detail at www.foaf-project.org/ which is incorporated herein by reference) and/or JSON data. The API call contains metadata about the request. For example, the metadata could be represented within the "application_data" key field and corresponding JSON payload shown in FIG. 5. The disclosure is not limited to the example in FIG. 5 and the system may utilize other types of metadata that the example shown in FIG. 5.

The data persistence system persists the user specific application data and API metadata in the graph database 114 as shown. The data persistence system correlates each persisted transaction to a unique identifier which tracks the provenance of the dynamic data fields. For example, FIG. 5 contains an example payload to be used in the correlation process. In the process, various correlation techniques may be used. For example, the correlation technique may include strong identifier linkage, partial or full document hashing, streaming weighted clustering, . . . etc.

Figure 3:
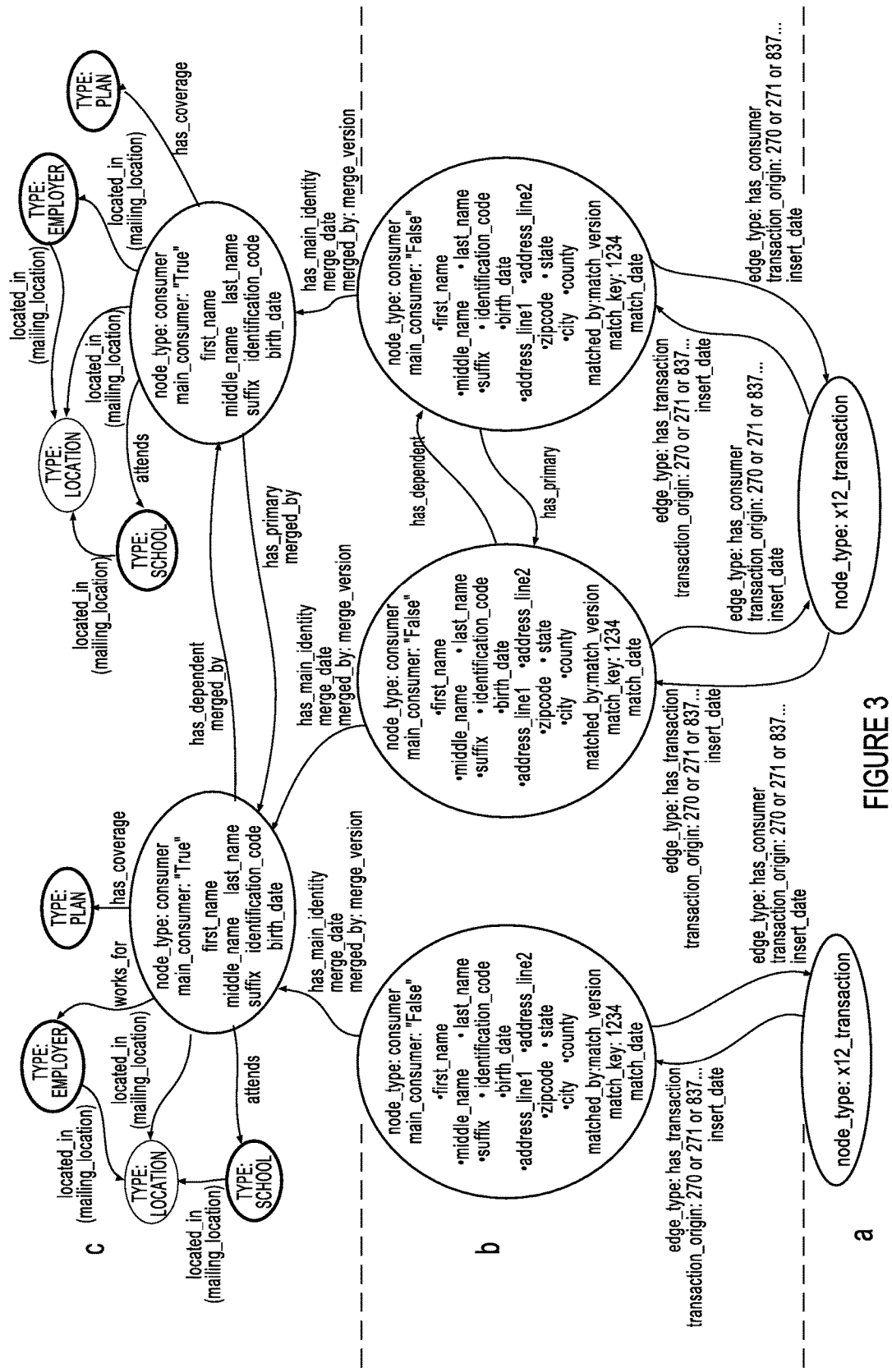
FIG. 3 illustrates an example of a health graph database that may be used by the data persistence system.
Figure 6:
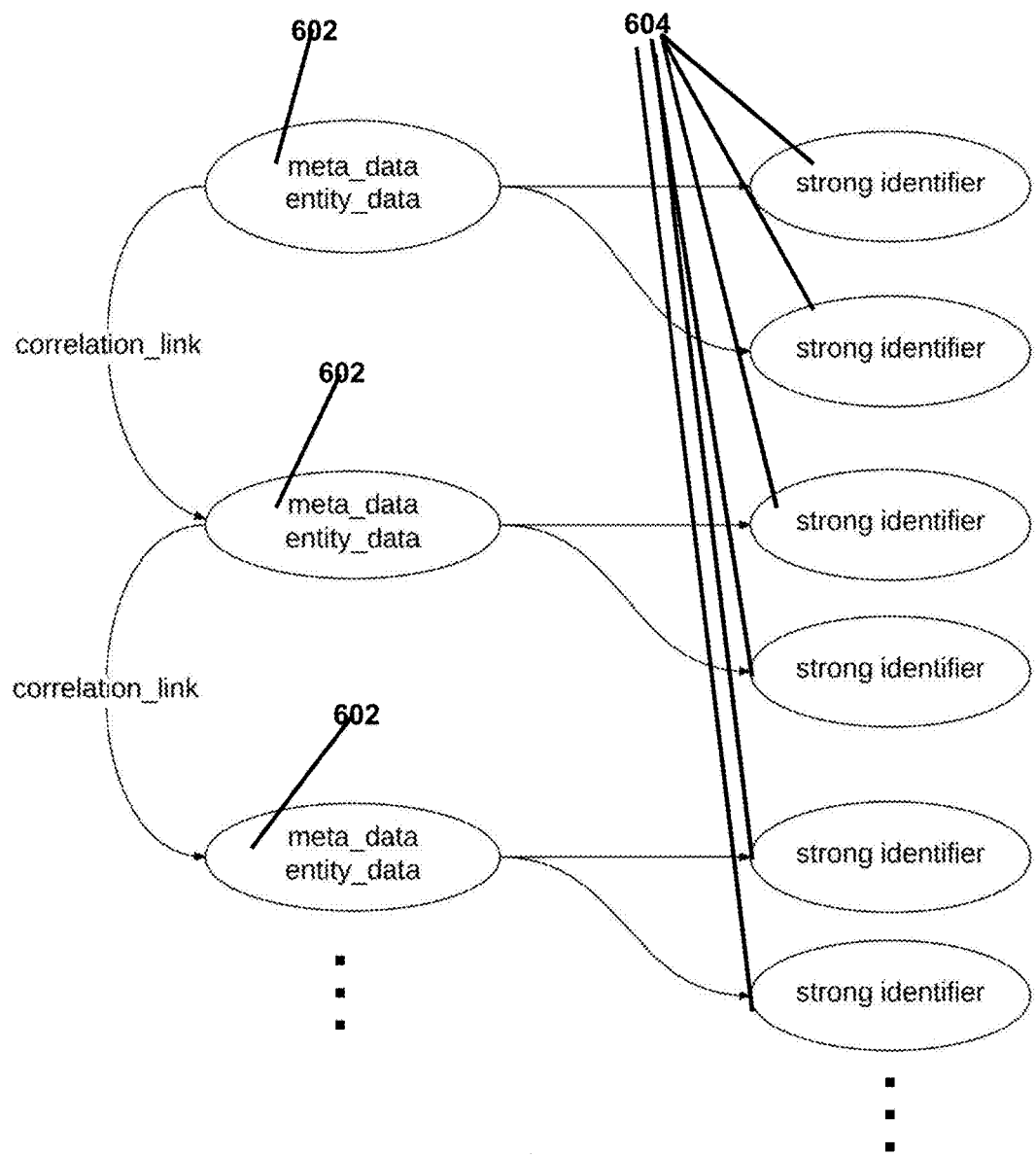
FIG. 6 illustrates the historical correlation linking process that is part of the data persistence method shown in FIG. 4.

The data persistence system utilizes this identifier to dynamically correlate the inflow of application data and metadata as shown in FIG. 2 to evolve the entities contained within the database (shown as a graph database for in the example in FIG. 2). An example of the evolving correlation process is shown in FIG. 6 and described below. FIG. 2 details the flow of this procedure from application level to data persistence and concludes with entity correlation. FIG. 3 illustrates an example of a health graph database that may be interfaced by the data persistence system and may be modified/updated by the data persistence system.

Figure 4:
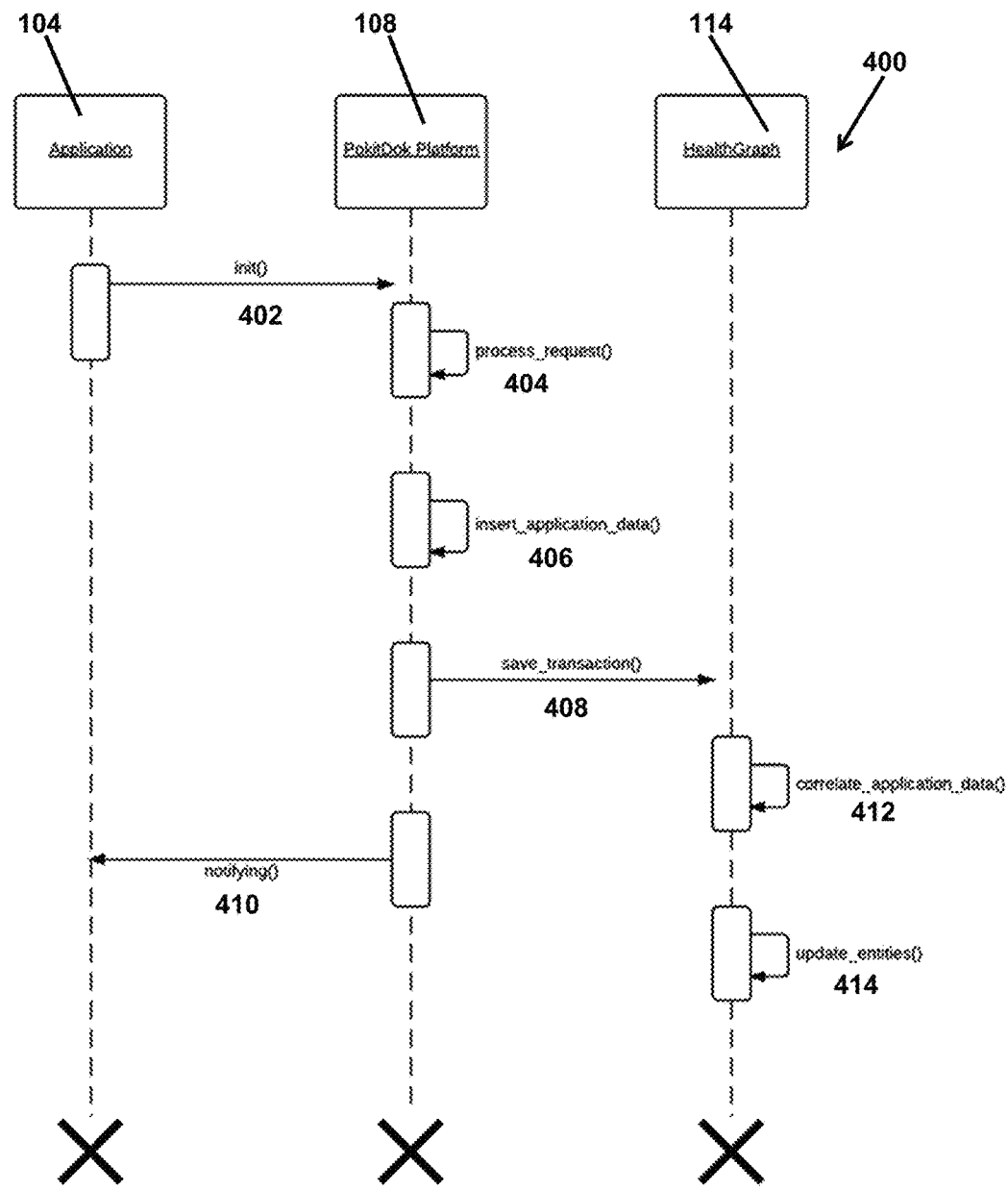
FIG. 4 details an example of a method for data persistence using the system having the three portions of the architecture shown in FIGS. 1-2.

FIG. 4 details an example of a method 400 for data persistence using the system having the three portions of the architecture shown in FIGS. 1-2. As shown, the method may be performed/implemented with the application 104 executed on a computing system, the backend system 108 and the healthgraph 114. Initially, an application 104 initializes the system through an API request (402—init( )). An example of this API request is described above. In the API request, the user declares application specific data (application level data) in the API call which is processed by the system 108 in FIGS. 1 and 2. The system 108 processes the API call and transforms it for the intended internal recipient (404—process_request( )). When an API call is received at the backend 108, it is transformed into an internal data model and run against an ensemble of correlation metrics that are executed by the streaming API processor 110. The data from the API may then be further combined with known data models from the health marketplace 112 and the input data stream is connected to the evolving entity (as described below) which is stored in the evolving entity persistence database 114.

Figure 7A:
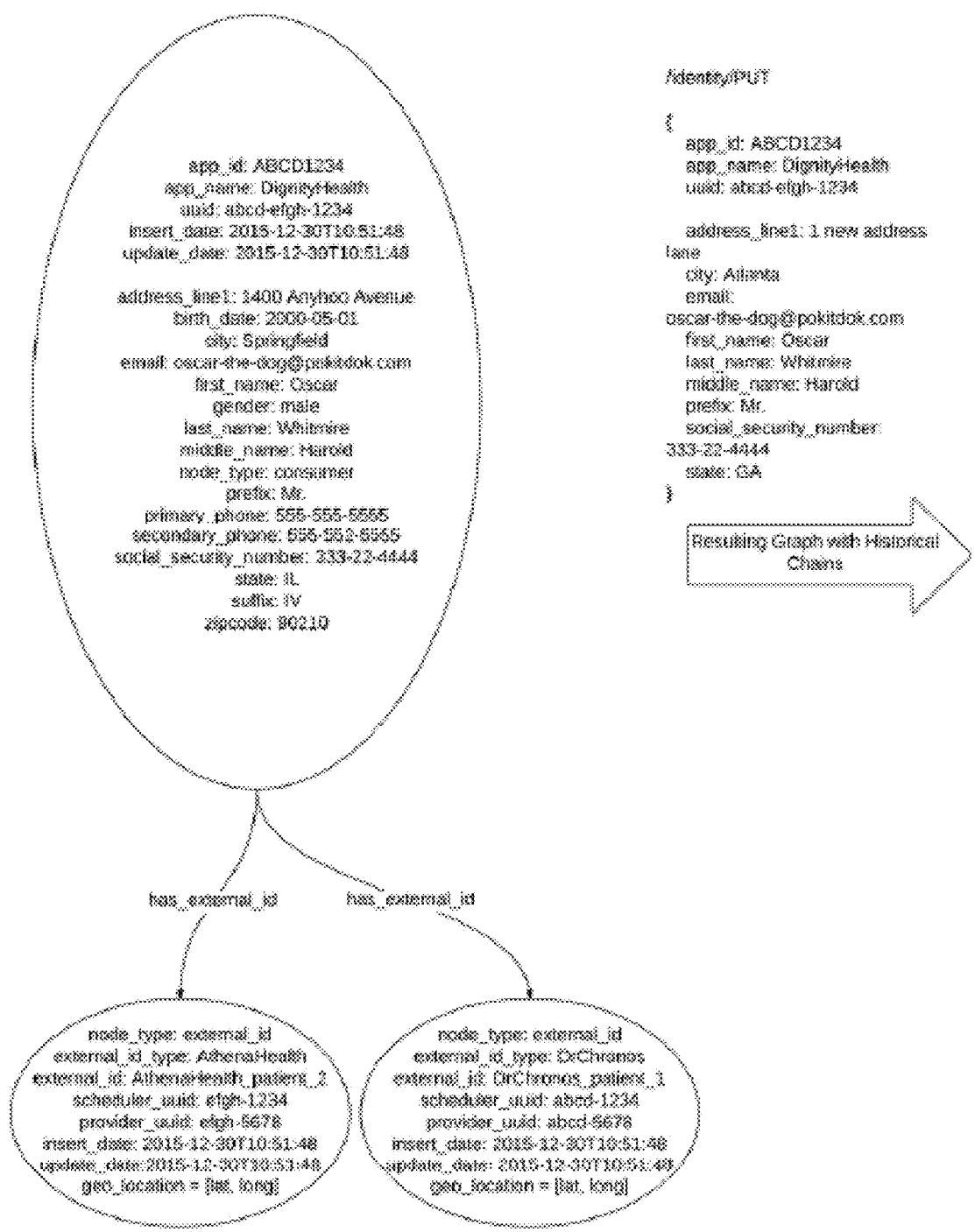
FIGS. 7A and 7B illustrate an example of the dynamic provenance tracking that occurs during the correlation process.
Figure 7B:
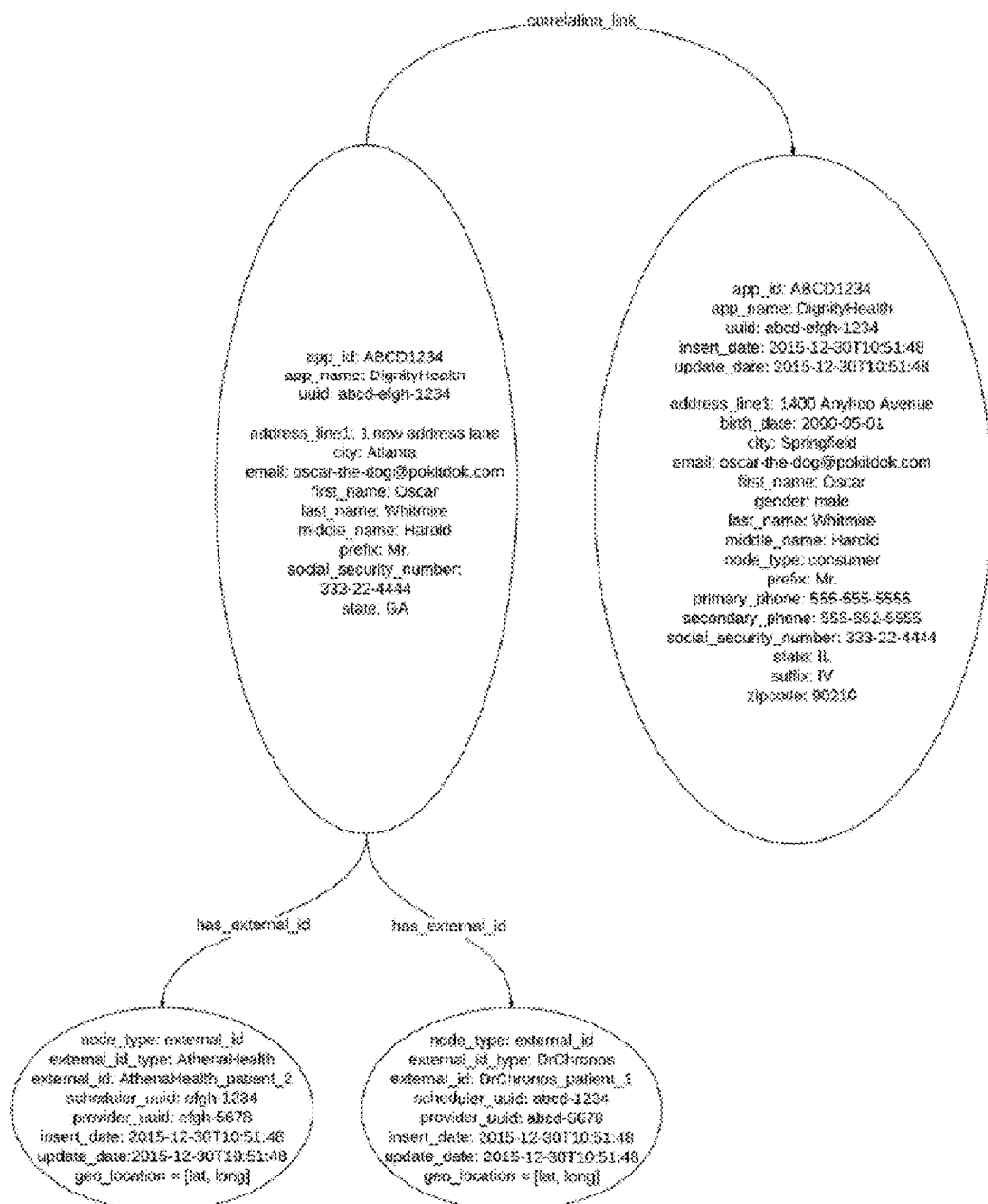

The system 108 may then appends the user specific data fields and API metadata fields to the internal transfer (406—insert_application_data( )). An example of the appending of the data fields to the internal transfer and extraction of the identity models from a data stream and correlation to a known identity is shown in FIGS. 7A and 7B where FIG. 7A shows an example of the known identity and the data fields from the API call and FIG. 7B shows the correlation of the data fields in the API call to the known entity.

In the method, the backend system 108 may persist this data in an internal database (408—save_transaction( )) and a unique identifier that tracks the provenance of the dynamic data fields. The unique identifier created for each observed entity can be vector of length n which represents the centroid of the entity's correlated data payloads. As additional payloads are processed and linked, this unique identifier, which can be represented as a centroid vector, is adjusted to account for the appended data. The chaining and linking process is shown in FIG. 6 and the features observed and correlated in FIGS. 7A and 7B represent the evolution of the vector space and the calculable entity centroid for dynamic provenance tracking.

During this process, the fields of the data may be checked against a whitelist for permitted external data fields and persisted according to each key's level of accessibility. The whitelist is autonomously updated to learn, identify and pass user specific fields. Once the database has received and persisted the immutable transaction based on the application level data and the metadata, a process is initialized which will update internal data models via the transactions unique identifier as shown for example in FIGS. 7A and 7B. Furthermore, as additional streaming entities are processed, they are linked to the existing entities which are calculated to have the highest match. This process extracts the application specific data and API metadata and correlates the data from the single request to the entities which it contains (412—correlate_application_data( )). The internal data models are updated and evolved according to the newly observed application data and metadata (414—update_entities( )). In the process, once the data has been saved into the health graph 114, the system 108 may notify the application 104 that the process has been completed (410—notifying( )).

FIG. 5 illustrates a level to which application level users can provide custom fields for persistence in the graph database. In particular, FIG. 5 shows that the system allows for dynamic key value declaration at the API endpoint in the application_data field. The API interface allows for custom key value pairs in this field which, when combined with the metadata from the transaction, are persisted in the database. For example, the transaction's activity_id is used to correlate the dynamic key/values pairs across the transaction database that is part of the health graph database 114. This data is correlated and joined to update the identity of each entity present within the transaction.

FIG. 6 illustrates the evolving correlation process. As payloads 602 are processed in a streaming manner, they are linked with existing and known strong identifiers 604. Simultaneously, these streaming payloads are measured for correlation according to the observed meta data and optimized correlation algorithm as described above. An example payload with strong identifers and meta data for correlation is shown in FIG. 5.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

The invention claimed is:

1. A system, comprising:
   a graph database that stores data about one or more entities associated with a healthcare computer system, the graph database having one or more nodes and one or more edges connecting each node and each node storing data about an entity and having a unique identifier of the entity;
   the healthcare computer system having a processor, memory and a plurality of instructions that is configured to:
   receive an application programming interface call containing application level data for a request for the entity and metadata about the request;
   a data persistence computer system, coupled to the healthcare computer system, having a processor, memory and a plurality of instructions that is configured to:
   persist the application level data and the metadata for the entity from the application programming interface call into the graph database and correlate, using the unique identifier of entity, each piece of persisted application level data and metadata to the entity already stored in the graph database; and
   wherein the entity already stored in the graph database is updated to include the correlated persisted application level data and metadata.

2. The system of claim 1, wherein the healthcare computer system receives data about a health care transaction through the API call.

3. The system of claim 2, wherein the data about a health care transaction is one of a X12 data format, a HL7 data format, a FHIR data format, a FOAF data format and a JSON data format.

4. The system of claim 1, wherein the data persistence computer system correlates each piece of persisted application level data to a unique identifier in the graph database to correlate the persisted application level data.

5. The system of claim 4, wherein the data persistence computer system tracks a provenance of the application level data using the unique identifier.

6. A data persistence method, comprising:
   providing a graph database that stores data about one or more entities associated with a healthcare computer system, the graph database having one or more nodes and one or more edges connecting each node and each node storing data about an entity and having a unique identifier of the entity;
   receiving, at a healthcare computer system, application level data for a request for the entity through an application programming interface call, the application programming interface call having metadata about the request;
   persisting, in the graph database that is part of the healthcare computer system, the application level data and the metadata for the entity from the application programming interface call;
   correlating, in a data persistence computer system coupled to the healthcare computer system, each piece of persisted application level data and metadata using the unique identifier of entity to the entity already stored in the graph database; and updating, by the healthcare computer system, the entity already stored in the graph database to include the correlated persisted application level data and metadata.

7. The method of claim 6, wherein receiving the application level data further comprises receiving data about a health care transaction.

8. The method of claim 7, wherein the data about a health care transaction is one of a X12 data format, a HL7 data format, a FHIR data format, a FOAF data format and a JSON data format.

9. The method of claim 6, wherein correlating each piece of persisted application level data and metadata further comprises correlating each piece of persisted application level data to a unique identifier in the graph database to correlate the persisted application level data.

10. The method of claim 9, wherein corrected each piece of persisted application level data to a unique identifier further comprises tracking a provenance of the application level data using the unique identifier.

* * * * *